United States Patent [19]

Schuster

[11] Patent Number: 5,735,277
[45] Date of Patent: Apr. 7, 1998

[54] METHOD OF PRODUCING AN ENDOPROSTHESIS AS A JOINT SUBSTITUTE FOR KNEE-JOINTS

[76] Inventor: Luis Schuster, Ringstr. 15, D 86911 Riederau, Germany

[21] Appl. No.: 530,829

[22] Filed: Sep. 20, 1995

[30] Foreign Application Priority Data

Sep. 27, 1994 [DE] Germany .............. 44 34 539.9

[51] Int. Cl.$^6$ ............................................. A61B 6/00
[52] U.S. Cl. ............................ 128/653.1; 128/653.2; 623/20
[58] Field of Search ................ 128/653.1, 653.2; 623/16, 18, 20, 66

[56] References Cited

U.S. PATENT DOCUMENTS

| | | | |
|---|---|---|---|
| 4,436,684 | 3/1984 | White | 128/653.1 |
| 4,506,393 | 3/1985 | Murphy | 128/653.1 |
| 4,650,490 | 3/1987 | Figgie, III | |
| 4,658,808 | 4/1987 | Link | |
| 4,759,350 | 7/1988 | Dunn et al. | |
| 4,976,737 | 12/1990 | Leake | |
| 5,370,692 | 12/1994 | Fink et al. | 623/16 |

FOREIGN PATENT DOCUMENTS

| | | |
|---|---|---|
| 0 255 797 | 2/1988 | European Pat. Off. |
| 32 13 434 | 4/1982 | Germany |
| 34 17 609 | 11/1985 | Germany |
| 35 22 196 | 2/1986 | Germany |
| 36 26 549 | 2/1988 | Germany |

OTHER PUBLICATIONS

"MG II Total Knee System Surgical Technique Using Zimmer® Intramedullary Instrumentation," Introduction, p. 1.

*Primary Examiner*—Ruth S. Smith
*Attorney, Agent, or Firm*—Ratner & Prestia

[57] ABSTRACT

In a process of producing an endoprosthesis as a joint replacement especially for knee joints, a reference image for determining contour differences on the femur and the tibia, which are obtained by comparing a corrected preoperative image of the damaged knee joint with a postoperative image, is used as the basis for preparing corresponding femoral and tibial components of the endoprosthesis.

7 Claims, No Drawings

METHOD OF PRODUCING AN ENDOPROSTHESIS AS A JOINT SUBSTITUTE FOR KNEE-JOINTS

BACKGROUND OF THE INVENTION

The present invention pertains to a process of producing an endoprosthesis as a joint replacement for knee joints, wherein the production of the prosthesis utilizes information from a surgical intervention on the femur, the tibia, and the patella of a damaged knee joint.

The surgical intervention on a knee joint is taken into consideration by the attending physician when the patient complains about severe pains in the knee and disability as a consequence of, e.g., rheumatoid arthritis or other joint diseases. The surgical intervention takes place conventionally in a plurality of steps, which are adapted exclusively to the shape of individual joint moldings, which are manufactured industrially in different graduated sizes and which are ultimately fastened to milled surfaces mainly of the anterior femoral condyle, of the distal femur, of the proximal tibia, and of the patella in such a way that a vertical alignment is achieved with such components in relation to an axis which is obtained, e.g., by means of a preoperative X-ray image and an intramedullary pin alignment system for the straight line connecting the center of the hip, the knee and the malleolus. An illustrative representation of such a surgical procedure can be found, e.g., in prospectus No. 97-5110-102 20 MA of the firm of Zimmer, Inc., 1989 edition, entitled "MG II TOTAL KNEE SYSTEM SURGICAL TECHNIQUE" as well as in U.S. Pat. No. 4,759,350, in which a corresponding intramedullary pin system is described.

Not only is the implantation of such three-part knee joint endoprostheses very expensive, but, taking into account the often great differences in the patients' growth, only an approximate restoration of the conditions of a healthy knee joint is achieved at best. Therefore, complications also occur frequently; they can be attributed to the mechanics of the implanted prosthesis components, and thus they lead, e.g., to an anterior knee joint pain syndrome, which is caused by incorrect gliding of the patella, with a nonphysiological loading of the femur-patella gliding joint. Irritations also frequently develop, occasionally with considerable hypertrophy of the joint mucosa and pronounced effusions in the knee joint as a consequence of a massive abrasion of the implanted prosthesis parts, some of which consist of polyethylene and will then lead to unfavorable gliding behavior with this material if such abrasion becomes excessive or loosening of the bone anchoring of the components of the prosthesis occurs, which is usually performed by means of pins and a screw connection and often with cementing. When such complications are determined, it is frequently necessary to implant a new endoprosthesis, in which case new problems arise, e.g., concerning the creation of a changed support for the components of a new prosthesis, with the requirement of a resection of additional bone parts.

SUMMARY OF THE INVENTION

The basic object of the present invention is therefore to provide a process of producing an endoprosthesis as a joint replacement especially for knee joints, which helps minimize the complications which can be observed in the case of the conventional implantation of such endoprostheses, e.g., the nonphysiological loading of the joint, the problem of a sufficient possibility of anchoring especially of the femoral and tibial components of the prosthesis, and the avoidance of an excessive loss of bone primarily at the time of the first implantation of such an endoprosthesis as a joint replacement for knee joints.

DESCRIPTION OF THE INVENTION

This object is accomplished with a process of producing an endoprosthesis as a joint replacement especially for knee joints by making use of the following steps:

1. A preoperative image of the patient's damaged knee joint is prepared. The preparation of such an image may be performed by computed tomography, i.e., a tomographic method, or preferably by nuclear magnetic resonance tomography, because it makes possible an especially sharp definition of the joint contour by representing the cartilaginous tissue and other soft parts of the damaged knee joints, so that correspondingly optimal preconditions are also created for the surgical intervention.

2. The surgical intervention is performed on the femur, the tibia, and the patella of the damaged knee joint subsequent to the preparation of such a preoperative image. Basically only the complete removal of the non-load-bearing bone and additionally the removal of only an absolute minimum of the adjacent healthy bone at least on the femur and the tibia have to be performed during this surgical intervention, so that a resection surface which is ideal for a subsequent cementing of the corresponding femoral or tibial component of the endoprosthesis to be implanted is obtained on the bone.

3. When the surgical intervention has been concluded, a corresponding postoperative image of the knee joint is prepared, again either by computed tomography or preferably by nuclear magnetic resonance tomography.

4. Subsequent to this surgical intervention or already subsequent to the preparation of the preoperative image of the damaged knee joint, a correction of this preoperative image is then performed, attempting to approach the conditions occurring in a healthy knee joint with this correction. This correction of the preoperative image may be performed either manually on this preoperative image itself, in which case the more or less ideal contours of at least the femur and of the tibia, which lead to a correspondingly optimal physiological joint contour of the knee joint for the joint surfaces provided with the endoprosthesis implanted later, are consequently followed with the correction. This correction of the preoperative image may therefore also be brought about, as an alternative, on the basis of an image which is, to the extent possible, a mirror image of a healthy knee joint opposite the damaged knee joint, based on the assumption that the two knee joints of a patient have identical shape and that the most favorable conditions for the implantation of the endoprosthesis can indeed be created for the damaged knee joint by such a comparison of a damaged knee joint with a healthy knee joint. It is also conceivable, in principle, to perform the correction of the preoperative image by a comparison with images of knee joints which were taken under comparable conditions, and the knee joints have joint surfaces of the femur, tibia and patella which are comparable with the damaged knee joint.

5. The preoperative image thus corrected is then compared with the postoperative image prepared subsequent to the surgical intervention in order to determine the differences between the two images. The conditions on the contours of the femur and tibia are of special interest in this connection, because the difference in the size of these contours is the basis for the subsequent preparation of corresponding femoral and tibial components of the endoprosthesis.

6. As was indicated above, the last process step of producing an endoprosthesis as a joint replacement for knee joints thus pertains to the preparation of at least femoral and tibial components, which corresponds to the difference in the size of the surfaces which were imaged for the corrected preoperative conditions on the femur and the tibia, the difference being determined with the reference image. The preparation of such femoral and tibial components of an endoprosthesis, which is subsequently to be implanted, is carried out, e.g., by digitizing the reference image which determines the differences between the corrected preoperative image and the postoperative image and subsequently using it for preparing the components on a machine according to a copying process.

As a result of the process of producing an endoprosthesis as a joint replacement for knee joints, components are obtained which thus have the contours of the healthy knee joint or lead at most to slightly different joint contours, which are adapted to the current bone-soft tissue conditions and are at the same time correspondingly ideally adapted physiologically, and whose successful implantation will then depend more or less only on the quality of the anchoring of the components. Since a major risk of mechanical loosening can hardly be expected in the case of the implantation of such nearly ideal joint replacement components, cementless anchoring of the components on the femur and the tibia is suitable for their anchoring, and the surgical intervention on the damaged knee joint can already be accomplished—with respect to the individual adaptation of the joint conditions in a patient—concerning the additional removal of healthy bone, besides the complete removal of no longer load-bearing bone, such that physiologically satisfactory anchoring of the components of the endoprosthesis is achieved for the implantation.

If necessary, the preparation of an endoprosthesis also includes, of course, the preparation of a component, which is used for the patella of the damaged knee joint. The process can also be used for a surgical intervention on other joints, e.g., the ankle joint, if comparable conditions can be presumed.

I claim:

1. A method of producing an endoprosthesis as a joint replacement for knee joints comprising:
    preparing a preoperative tomographic image of the damaged knee joint;
    preparing a healthy knee joint tomographic image by approximating the contours of at least the femoral bone and the tibia of the damaged knee joint to those of a healthy knee joint;
    preparing a postoperative tomographic image of the damaged knee joint;
    comparing and determining the differences between: (1) the contours of at least the femoral bone and of the tibia of the healthy knee joint tomographic image; and (2) the contours of at least the femoral bone and of the tibia of the postoperative tomographic image of the damaged knee joint, to prepare a tomographic reference image representing said differences; and
    preparing at least a femoral component and a tibial component of an endoprosthesis based on the tomographic reference image.

2. The method of claim 1, wherein all of said tomographic images are prepared by a computed tomography.

3. The method of claim 1, wherein all of said tomographic images are prepared by a nuclear spin resonance tomography.

4. The method of claim 1, wherein the step of preparing said healthy knee joint tomographic image comprises manually altering said preoperative tomographic image.

5. The method of claim 1, wherein the step of preparing said healthy knee joint tomographic image includes preparing a mirror image of a healthy knee joint of the patient.

6. The method of claim 1, wherein the step of preparing said healthy knee joint tomographic image includes identifying an image of a healthy knee joint having contours of at least the femoral bone and the tibia comparable to the contours of the preoperative image of the damaged knee joint.

7. The method of claim 1, wherein the step of preparing at least a femoral component and a tibial component of an endoprosthesis includes digitizing the reference image and using said digitized reference image to prepare said femoral component and said tibial component according to a copying process.

* * * * *